United States Patent [19]

Hönel et al.

[11] 4,143,016

[45] Mar. 6, 1979

[54] PREPARATION OF MELAMINE DERIVATIVES

[75] Inventors: Hans Hönel, Frankfurt am Main; Karlfried Keller, Bergen-Enkheim; Walter Michel, Frankfurt am Main; Manfred Schön, Rodgau, all of Fed. Rep. of Germany

[73] Assignee: Cassella Aktiengesellschaft, Frankfurt, Fed. Rep. of Germany

[21] Appl. No.: 875,307

[22] Filed: Feb. 6, 1978

[30] Foreign Application Priority Data

Apr. 9, 1977 [DE] Fed. Rep. of Germany ....... 2716006

[51] Int. Cl.² ............................................. C08L 61/28
[52] U.S. Cl. .............................. 260/29.4 R; 528/239; 528/243; 528/254
[58] Field of Search ...................... 260/67.6 R, 29.4 R; 528/243, 239, 254

[56] References Cited

U.S. PATENT DOCUMENTS 3,087,837  4/1963  Van Loo et al. ............... 260/67.6 R

FOREIGN PATENT DOCUMENTS 674948   7/1952  United Kingdom ............... 260/67.6 R
1030268  5/1966  United Kingdom ............... 260/67.6 R

*Primary Examiner*—M. J. Welsh
*Attorney, Agent, or Firm*—Connolly and Hutz

[57] ABSTRACT

A process for the preparation of a substantially monomeric methylolmelamine etherified by methanol which contains per mol of melamine, more than 5 mols of formaldehyde and more than 4 mols of methyl-etherified methylol groups which has a viscosity of less than 10 Pa.s at 25° C. at a solids content of at least 95%, said process comprising reacting melamine and formaldehyde in a molar ratio of from 1 : 6.2 to 1 : 8, at a temperature of from 40 to 60° C., in the presence of a basic catalyst in a reaction mixture which contains from 10 to 40% by weight of water and from 40 to 20% by weight of methanol thereby producing a suspension of methylolmelamine, and then etherifying the methylol melamine in the presence of from 15 to 30 mols of methanol per mol of melamine, at a temperature of from 25 to 50° C., in the presence of a strong acid.

5 Claims, No Drawings

PREPARATION OF MELAMINE DERIVATIVES

The invention relates to a process for the manufacture of substantially monomeric methyl-etherified methylol melamines which contain, per mol of melamine, more than 5 mols of formaldehyde and more than 4 mols of methyletherified methylol groups and, at a solids content of at least 95%, have a viscosity of less than 10 Pa.s* at 25° C.

*In accordance with the SI-system (Système International d'Unité) the dynamic viscosity unit is the Pascal-second having the unit symbol: Pa.s. 1 Pascal-second equals the dynamic viscosity of a laminar-flowing, homogeneous fluid wherein between two plane layers thereof being parallel-arranged at 1 m interval and having a difference in speed of 1 m/s there exists 1 Pascal shearing stress. Between the Poise unit hitherto used and the Pascal-second unit there is the relationship of 1 Poise = 0.1 Pa.s.

Melamine resins of this type are used, for example, as so-called high-solid lacquer resins for the manufacture of lacquers. Because of their low viscosity, coupled, at the same time, with relatively high solids contents, the lacquers need to contain only small amounts of volatile solvents under the processing conditions. As a result, the amounts of volatile organic solvents liberated during processing, for example during the stoving of sprayed-on stoving lacquers, are also only small, which is highly desirable for protection of the environment.

According to British Pat. Spec. No. 1,030,268, melamine resins of this type can be manufactured by methylolation of melamine with more than 10 mols of paraformaldehyde per mol of melamine in methanolic solution in the presence of a basic catalyst and subsequent etherification with excess methanol in the presence of a strong inorganic acid. Since at most 6 mols of formaldehyde are bonded per mol of melamine, either the formaldehyde present in excess gives rise to a severe load on the effluent and exhaust air, or the formaldehyde present in excess has to be worked up at additional cost. If, instead of the more than 10 mols of paraformaldehyde mentioned in Example 1 of the above patent specification, 7 mols of paraformaldehyde are employed per mol of melamine, products are obtained which, as a result of a higher degree of condensation and lower degree of etherification, are more highly viscous and, at a solids content of 95%, have a viscosity of more than 1,500 Pa.s. In addition, the melamine resins manufactured in this way have only a lesser stability and a reduced compatibility with hydrophobic components and, as a result, are not very suitable as so-called high-solid lacquer resins.

In U.S. Pat. No. 2,918,452, a process for the manufacture of substantially monomeric methyl-etherified melamine resins is described, according to which methylolation with, for example, 7 mols of paraformaldehyde per mol of melamine in the presence of xylene and subsequent acid etherification with excess methanol, either in the presence of the xylene or after removal of the xylene, is possible. In addition to the use of paraformaldehyde, which is obtained in a technically involved manner by concentrating aqueous formaldehyde solutions, disadvantages of this process which may be mentioned are, in particular, the comminution of the crystalline methylolmelamine which is obtained as an intermediate product and the use of xylene, which constitutes a fire hazard and pollutes the environment, the use of xylene also lowering the space-time yield.

In order to manufacture substantially monomeric methyl-etherified methylolmelamines it is also known to react melamine with aqueous formaldehyde solutions. The methylolmelamine intermediate products separated out in this process must, however, be isolated prior to the subsequent etherification and either these intermediate products must be dried (U.S. Pat. Nos. 2,998,410, 3,020,255 and 3,087,837) or the moist intermediate product must be subjected to an etherification in two stages (U.S. Pat. No. 2,998,411), in which case an entraining agent, such as xylene or toluene, usually also has to be added at the end of the first etherification stage. The necessary isolation of the intermediate product is a particular disadvantage of these processes.

Finally, a process for the manufacture of substantially monomeric methyl-etherified melamine resins is also known from British Patent Specification No. 674,948, and in this process melamine is methylolated with 8 mols of aqueous formaldehyde solution per mol of melamine and then etherified with methanol in the presence of a strong inorganic acid. The melamine resins manufactured by this process are, however, highly viscous at 25° C. and at a solids content of 95% and have a viscosity of more than 1,000 Pa.s.

The object of the invention was, therefore, to avoid the disadvantages of the previous processes for the manufacture of substantially monomeric methyl-etherified methylolmelamines, which contain, per mol of melamine, more than 5 mols of formaldehyde and more than 4 mols of methyl-etherified methylol groups and, at a solids content of at least 95%, have a viscosity of less than 10 Pa.s at 25° C. According to the invention, this object is achieved by reacting melamine and formaldehyde in a molar ratio of 1:6.2 to 1:8, at temperatures of 40° to 60° C., in the presence of a basic catalyst in a reaction mixture which contains 10 to 40% by weight of water and 40 to 20% by weight of methanol, to give a suspension of methylolmelamine and then etherifying the latter in the presence of a total of 15–30 mols of methanol per mol of melamine at temperatures of 25° to 50° C. in the presence of a strong acid.

The process according to the invention is preferentially suitable for the manufacture of those substantially monomeric methyl-etherified methylolmelamines which contain, per mol of melamine, more than 5.5 mols of formaldehyde and 4.3 to 5.1 mols of methyl-etherified methylol groups.

In the process according to the invention, formaldehyde is employed in the form of the conventional aqueous or methanolic solution or of an aqueous-methanolic solution, optionally together with paraformaldehyde, and 6.2 to 8 mols, and preferably 6.5 to 7 mols, of formaldehyde must be present per mol of melamine.

Inorganic or organic bases or compounds having a basic reaction, such as, for example, triethylamine, alkali metal carbonates, such as, for example, potassium carbonate or sodium carbonate, alkali metal bicarbonates, such as, for example, sodium bicarbonate, or alkali metal hydroxides, such as, for example, sodium hydroxide solution or potassium hydroxide solution, can be used as the basic catalyst for the methylolation. Sodium hydroxide solution is preferably used. Amounts of 0.1 to 1% by weight, and preferably of 0.2 to 0.5% by weight, of the base or compound having a basic reaction are employed, relative to the weight of the starting components melamine and formaldehyde.

According to the invention, water and/or methanol are added in an amount such that the reaction mixture contains 10 to 40% by weight of water and 40 to 20% by weight of methanol during the methylolation. The ratio between water and methanol is so chosen that the reaction mixture contains 50 to 60% by weight of the water/methanol mixture.

The methylolation is carried out at temperatures of 40° to 60° C., preferably at 45° to 55° C., in the course of 1 to 5 hours and preferably of 2-4 hours. The reaction batch is stirred during the methylolation.

According to the process of the invention, a readily stirrable suspension of highly methylolated melamine is obtained which subsequently can be etherified in the same reaction vessel without isolation and intermediate drying.

For etherification, methanol is added to the resulting suspension in an amount such that a total of 15 to 30 mols of methanol are present per mol of melamine. The etherification is carried out, whilst stirring, at temperatures of 25° to 50° C., and preferably 30° to 40° C., in the presence of 1 to 10% by weight of a strong acid, relative to the weight of the starting components. Suitable strong acids can be mineral acids, such as, for example, sulphuric acid, hydrochloric acid or phosphoric acid, carboxylic acids, such as, for example, trichloroacetic acid, or sulphonic acids, such as, for example, p-toluenesulphonic acid. Nitric acid is preferably used. Depending on the reaction conditions, the etherification has ended after 20 minutes to 2 hours maximum. After etherification has ended, a clear solution has formed.

Subsequently, the batch is worked up in a known manner, that is to say, for example, neutralised or rendered slightly alkaline with sodium carbonate or potassium carbonate, sodium hydroxide or potassium hydroxide and the excess methanol, together with the water contained in the batch, is distilled off in vacuo. After all of the volatile constituents have been removed, the melamine resin is filtered, for example through kieselguhr, in order to separate off the salt.

If the methanol content of the reaction mixture is raised to more than 40% by weight during the methylolation, more than 8 mols of formaldehyde per mol of melamine must be employed in order to manufacture methyl-etherified methylolmelamines of low viscosity, because of increased hemi-acetal formation. However, this procedure is uneconomical and not very favourable in respect of environmental protection. A methanol content lower than 20% by weight of the reaction mixture during the methylolation gives rise to a highly exothermic reaction at the start of the methylolation and to the formation of lumpy methylolmelamines which subsequently can be etherified only with difficulty to end products having viscosities of less than 10 Pa.s. The methylolmelamines manufactured by the process according to the invention, the reaction mixture for which contains 40-20% by weight of methanol, are obtained in the form of readily stirrable mixtures of low viscosity which can be etherified without difficulty.

The etherified methylolmelamines manufactured by the process according to the invention have a viscosity of less than 10 Pa.s at 25° C. with a solids content of at least 95%. This low viscosity is achieved by the use of at least 6.2 mols of formaldehyde per mol of melamine. Methoxymethyl-melamines manufactured using more than 8 mols of formaldehyde per mol of melamine do not have any improved properties compared with the products manufactured within the molar ratios claimed. When less than 6.2 mols of formaldehyde are employed per mol of melamine, more highly viscous melamine resins are formed as a result of incompletely methylolated intermediate products undergoing a condensation reaction. Methyl-etherified methylolmelamines of particularly low viscosity are obtainable with amounts of from 6.5 mols of formaldehyde per mol of melamine; up to a molar ratio of melamine:formaldehyde of 1:7, end products which do not pollute the environment and produce only a slight load on the effluent and exhaust air are formed.

The process according to the invention is a simple and economical one-pot process which does not pollute the environment and, in a single stage etherification, gives substantially monomeric methyl-etherified methylolmelamines of low viscosity without the use of a large excess of formaldehyde, without the addition of an inert solvent and without intermediate drying of water-containing methylolmelamines.

The products obtained by the process according to the invention can be used, for example, for finishing textiles and paper and also for the high-solid field of lacquer-coating in combination with alkyd resins, oil-free polyesters or acrylate resins for the production of high-gloss, scratch-resistant coatings which have very good resistance to weathering, and also as adhesives. If the addition of solvents is necessary when the products are used, it is necessary to add only small amounts, because of the low viscosity of the products.

The examples which follow serve to illustrate the invention further. Percentage data are data in percentages by weight.

EXAMPLE 1

| Molar ratio | melamine | : | formaldehyde | : | methanol |
|---|---|---|---|---|---|
| | 1 | : | 7 | : | 22 |

The pH of 159 parts by weight of a 39% strength aqueous formaldehyde solution is adjusted to 7 with sodium hydroxide solution in a 2 liter three-necked flask. 165 parts by weight of paraformaldehyde (90% strength, remainder water), 243 parts by weight of methanol, 126 parts by weight of melamine and 1.5 ml of 50% strength sodium hydroxide solution are then added and the contents of the flask are stirred at 50° C. for 2 hours, during which time a readily stirrable slurry forms. The reaction mixture contains 16.6% of water and 35% of methanol. After cooling, 461 parts by weight of methanol are added, and at 30° C. 37 parts by weight of 55% strength nitric acid are added. Etherification is then carried out at 35° C. for about 25 minutes, whilst stirring, and a clear solution forms; the pH of this solution is immediately adjusted to 8.5 with sodium hydroxide solution and the mixture is concentrated under a waterpump vacuum until the internal temperature is 85° C. and is then filtered hot through kieselguhr.

The resulting 95% strength methyl-etherified methylolmelamine (the solids content is calculated from the loss in weight which 2 g of the product undergo on heating for one hour at 120° C. in an aluminium dish) has a viscosity of 4.8 Pa.s at 25° C. and contains about 5.9 mols of formaldehyde and about 4.8 mols of methyl-etherified methylol groups per mol of melamine.

EXAMPLE 2

| Molar ratio | melamine | : | formaldehyde | : | methanol |
|---|---|---|---|---|---|
| | 1 | : | 6.5 | : | 25 |

The pH of 147 parts by weight of a 39% strength aqueous formaldehyde solution is adjusted to 7 with sodium hydroxide solution in a 2 liter three-necked flask. 153 parts by weight of paraformaldehyde (90% strength, remainder water), 243 parts by weight of methanol, 126 parts by weight of melamine and 1.5 ml of 50% strength sodium hydroxide solution are then added and the contents of the flask are stirred at 50° C. for 3 hours, and a readily stirrable slurry forms. The reaction mixture contains 15.8% of water and 36.2% of methanol.

After cooling, 557 parts by weight of methanol are added and at 30° C. 37 parts by weight of 55% strength nitric acid are added. The batch is then further processed as in Example 1.

The resulting 95% strength methyl-etherified methylolmelamine has a viscosity of 8.7 Pa.s at 25° C. and contains about 5.6 mols of formaldehyde and about 4.5 mols of methyl-etherified methylol groups per mol of melamine.

EXAMPLE 3

| Molar ratio | melamine | : | formaldehyde | : | methanol |
|---|---|---|---|---|---|
| | 1 | : | 8 | : | 25 |

The pH of 410 parts by weight of a 39% strength aqueous formaldehyde solution is adjusted to 7 with sodium hydroxide solution in a 2 liter three-necked flask. 88.7 parts by weight of paraformaldehyde (90% strength, remainder water), 298 parts by weight of methanol, 126 parts by weight of melamine and 1.5 ml of 50% strength sodium hydroxide solution are then added and the contents of the flask are stirred at 45° C. for 3 hours, and a readily stirrable slurry forms. The reaction mixture contains 28.1% of water and 32.2% of methanol. After cooling, 502 parts by weight of methanol are added, and at 30° C. 37 parts by weight of 55% strength nitric acid are added. The batch is then further processed as in Example 1.

The resulting 95% strength methyl-etherified methylolmelamine has a viscosity of 7.4 Pa.s at 25° C. and contains about 5.9 mols of formaldehyde and about 4.7 mols of methyl-etherified methylol groups per mol of melamine.

EXAMPLE 4

| Molar ratio | melamine | : | formaldehyde | : | methanol |
|---|---|---|---|---|---|
| | 1 | : | 7 | : | 25 |

The pH of 538.5 parts by weight of a 39% strength aqueous formaldehyde solution is adjusted to 7 with sodium hydroxide solution in a 2 liter three-necked flask. 224 parts by weight of methanol, 126 parts by weight of melamine and 1.5 ml of 50% strength sodium hydroxide solution are then added and the contents of the flask are stirred at 55° C. for 3 hours, and a readily stirrable slurry forms. The reaction mixture contains 37% of water and 25.2% of methanol.

After cooling, 576 parts by weight of methanol are added, and at 30° C. 37 parts by weight of 55% strength nitric acid are added. The batch is then further processed as in Example 1.

The resulting 95% strength methyl-etherified methylolmelamine has a viscosity of 5.2 Pa.s at 25° C. and contains about 5.7 mols of formaldehyde and about 4.8 mols of methyl-etherified methylol groups per mol of melamine.

EXAMPLE 5

| Molar ratio | melamine | : | formaldehyde | : | methanol |
|---|---|---|---|---|---|
| | 1 | : | 7 | : | 25 |

The pH of 568 parts by weight of methanol-containing formaldehyde (37% of formaldehyde, 43% of methanol and 20% of water) is adjusted to 7 with sodium hydroxide solution in a 2 liter three-necked flask. 126 parts by weight of melamine and 1.5 ml of 50% strength sodium hydroxide solution are then added and the contents of the flask are stirred at 55° C. for 5 hours, and a readily stirrable slurry forms. The reaction mixture contains 16.5% of water and 35.1% of methanol.

After cooling, 555.8 parts by weight of methanol are added, and at 30° C. 37 parts by weight of 55% strength nitric acid are added. The batch is then further processed as in Example 1.

The resulting 95% strength methyl-etherified methylol melamine has a viscosity of 3.5 Pa.s at 25° C. and contains about 5.9 mols of formaldehyde and about 4.8 mols of methyl-etherified methylol groups per mol of melamine.

What we claim is:

1. A process for the preparation of a substantially monomeric methylolmelamine etherified by methanol which contains per mol of melamine, more than 5 mols of formaldehyde and more than 4 mols of methyl-etherified methylol groups which has a viscosity of less than 10 pascalseconds at 25° C. at a solids content of at least 95%, said process comprising reacting melamine and formaldehyde a molar ratio of from 1:6.2 to 1:8, at a temperature of from 40° to 60° C., in the presence of a basic catalyst in a reaction mixture which contains from 10 to 40% by weight of water and from 40 to 20% by weight of methanol thereby producing a suspension of methylolmelamine, and then without separating methylol melamine from the suspension etherifying the methylol melamine in the presence of from 15 to 30 mols of methanol per mol of melamine, at a temperature of from 25° to 50° C., in the presence of a strong acid.

2. A process according to claim 1, wherein melamine and formaldehyde are reacted together in a molar ratio of from 1:6.5 to 1:7.

3. A process according to claim 2 wherein melamine and formaldehyde are reacted at a temperature of from 45 to 55° C.

4. A process according to claim 1 wherein the etherification is carried out at a temperature of from 30° to 40° C.

5. A substantially monomeric methylolamine etherified by methanol which contains, per mol of melamine, more than 5 mols of formaldehyde and more than 4 mols of methyletherified methylol groups and which has a viscosity of less than 10 pa.s at 25° C. at a solids content of at least 95%, when prepared by the process according to claim 1.

* * * * *